US006555517B1

(12) United States Patent
Markert et al.

(10) Patent No.: US 6,555,517 B1
(45) Date of Patent: Apr. 29, 2003

(54) METHODS OF PROVIDING A FRAGRANCE TO A COMPOSITION AND METHODS OF ENHANCING FRAGRANCES USING CYCLOOCTADIENE HYDROFORMYLATION PRODUCTS

(75) Inventors: Thomas Markert, Monheim (DE); Volker Porrmann, Hilden (DE); Theo Ten Pierik, Le Venio (NL)

(73) Assignee: Cognis Deutschland GmbH, Duesseldorf (DE)

( * ) Notice: Subject to any disclaimer, the term of this patent is extended or adjusted under 35 U.S.C. 154(b) by 0 days.

(21) Appl. No.: 09/647,612

(22) PCT Filed: Mar. 25, 1999

(86) PCT No.: PCT/EP99/02018

§ 371 (c)(1),
(2), (4) Date: Dec. 6, 2000

(87) PCT Pub. No.: WO99/51713

PCT Pub. Date: Oct. 14, 1999

(30) Foreign Application Priority Data

Apr. 3, 1998 (DE) .......................................... 198 14 913

(51) Int. Cl.$^7$ .................................................. A61K 7/46
(52) U.S. Cl. ............................. 512/27; 512/25; 512/26
(58) Field of Search ................................ 512/25, 26, 27

(56) References Cited

U.S. PATENT DOCUMENTS

| 3,985,769 A | 10/1976 | Vesley et al. |
| 4,306,085 A | 12/1981 | Kim et al. |
| 4,317,936 A | 3/1982 | Kim et al. |

FOREIGN PATENT DOCUMENTS

| JP | 58/21638 A | 2/1983 |

OTHER PUBLICATIONS

Williams, D.F. and Schmutt, W.H.: "Chemistry and Technology of the Cosmetics and Toileteries Industry", 1996, Blackie Academic & Professional, London, XP002107027, p. 279.

A. Spencer, "Hydroformylation Of Cyclic Dienes Catalysed By Acetatocarbonylbis(triphenylphosphine) Rhodium (I)", Journal of Organometallic Chemistry, vol. 124, (1997), pp. 85–91.

Primary Examiner—Jill Warden
Assistant Examiner—Monique T. Cole
(74) Attorney, Agent, or Firm—John E. Drach; Aaron R. Ettelman

(57) ABSTRACT

The use of aldehydes as odorous materials, which can be produced through partial or total hydroformylation of cyclooctadienes, except cyclooctane aldehydes, is described. The fragrance enhancing capacity of the compounds is described in methods for their use both as perfumes and perfume enhancers or boosters.

14 Claims, No Drawings

METHODS OF PROVIDING A FRAGRANCE TO A COMPOSITION AND METHODS OF ENHANCING FRAGRANCES USING CYCLOOCTADIENE HYDROFORMYLATION PRODUCTS

BRIEF SUMMARY OF THE INVENTION

The present invention includes methods of using aldehydes obtainable by partial or complete hydoformylation of cyclooctadienes, excluding cyclooctane aldehyde, for providing fragrances to compositions and/or enhancing already existing fragrances.

The hydroformylation of cyclic dienes is known from the literature. For example, A. Spencer describes the hydroformylation of inter alia 1,3- and 1,5-cyclooctadiene in the presence of special rhodium catalysts in Journal of Organometallic Chemistry 1997, 124, pages 85 to 91. JP 58/21638 describes a process for the production of dialdehydes in which unconjugated diolefins are reacted with hydrogen and carbon monoxide in a water-immiscible solvent in the presence of a rhodium catalyst.

There is no information in the prior art literature on the olfactory properties of aldehydes or dialdehydes obtainable by hydroformylation of cyclooctadienes except for cyclooctane aldehyde. Only cyclooctane aldehyde (2a), which is described in U.S. Pat. No. 3,985,769 as a raw material for the production of acetal derivatives with perfume properties, is known for its olfactory properties which are described as "intensively green".

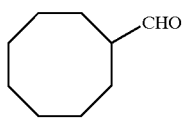

(2a)

Judging by demand, many natural perfumes are available in totally inadequate quantities. Accordingly, it is clear that there is a constant demand in the perfume industry for new perfumes with interesting perfume notes in order to extend the range of naturally available perfumes and to be able to make the necessary adaptations to changing fashion trends and to satisfy the continuously increasing demand for odor enhancers for products of everyday use, such as cosmetics and cleaning products.

In addition, there is generally a constant need for synthetic perfumes which can be favorably produced in a consistent quality and which have desirable olfactory properties, i.e. pleasant, near-natural and qualitatively new odor profiles of adequate intensity, and which are capable of advantageously influencing the fragrance of cosmetic and consumer products. In other words, there is a constant need for compounds which have characteristic new odor profiles coupled with high staying power, intensity of odor and emanative power.

BRIEF SUMMARY OF THE INVENTION

It has surprisingly been found that aldehydes obtainable by partial or complete hydroformylation of cyclooctadienes, except for cyclooctane aldehyde, have remarkable olfactory properties. Over and above their special odor characteristic, which is characterized by a broad range with complex nuances, the compounds are distinguished by high staying and emanative power. In addition, they are eminently suitable as perfume boosters. A perfume booster is understood to be a substance which is capable of lastingly intensifying the olfactory impressions of the components of a multicomponent system, i.e. a mixture of two or more perfumes.

The present invention relates to the use of aldehydes obtainable by partial or complete hydroformylation, of cyclooctadiene, with the exception of cyclooctane aldehyde, as perfumes.

The present invention also relates to the use of aldehydes obtainable by partial or complete hydroformylation of cyclooctadienes, with the exception of cyclooctane aldehyde, as perfume boosters. 4-Cyclo-octene aldehye is preferred for this use.

DETAILED DESCRIPTION OF THE INVENTION

The aldehydes to be used in accordance with the invention are advantageously prepared by hydroformylation of cyclooctadienes. Any cyclooctadienes of which the olefinic double bonds are not immediately adjacent may be used. Accordingly, suitable starting materials are 1,3-cyclooctadiene (1a), 1,4-cyclooctadiene (1b) and 1,5-cyclooctadiene (1c):

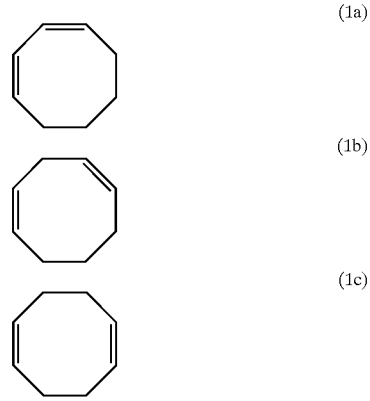

The hydroformylation is a reaction known to the expert which was discovered by Roelen in 1938. In this reaction, alkenes are converted into aldehydes with carbon monoxide and hydrogen. The reaction is also known as oxosynthesis. Since, as mentioned above, cyclooctadienes are used as starting materials for the purposes of the present invention, the hydroformylation may be carried out in part or completely. In the case of partial hydroformylation, one olefinic double bond remains intact while only the other is hydroformylated; in the case of complete hydroformylation, two CHO groups are introduced into the molecule.

The odor profile of the hydroformylation products according to the invention is original and novel. In perfume compositions, they enhance harmony and emanation and also staying power, the particular dosage being adapted to the perfume note required taking the other constituents of the composition into account.

The fact that the hydroformylation products according to the invention have interesting perfume notes was not foreseeable and is confirmation of the general experience that the olfactory properties of known perfumes are not necessarily an indication of the properties of structurally related compounds—in the present case cyclooctane aldehyde (2a) for example—or mixtures thereof because neither the mechanism of odor perception nor the influence of chemical structure on odor perception has been sufficiently researched, i.e. it cannot normally be predicted whether a modified structure or special mixing ratios of known perfumes lead at all to changes in the olfactory properties and whether these changes may be regarded as positive of negative.

By virtue of their odor profiles, the hydroformylation products according to the invention are also particularly suitable for modifying and enhancing known compositions. Particular emphasis is placed above all on their outstanding intensity of odor which contributes quite generally towards the refinement of compositions.

Also remarkable is the way in which the hydroformylation products according to the invention round off and harmonize the perfume notes of a broad range of known compositions without unpleasantly dominating them in any way.

4-Cyclooctene aldehyde.(2b), which in undiluted form has an almost unpleasantly strong smell and of which the odor is reminiscent of freshly harvested potatoes, is most particularly suitable for use as a perfume and/or perfume booster in accordance with the invention. Accordingly, it is of particular advantage to use 4-cyclooctene aldehyde in air fresheners for example. In addition, it has been found that 4-cyclooctene aldehyde may be used with particular advantage for enhancing citrus notes in cleaning compositions. In this connection, reference is made by way of example to acitecus composition, as set forth in the Examples below.

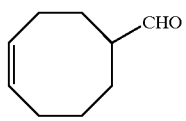
(2b)

4-Cyclooctene aldehyde (2b), for which another chemical name is 5-formyl-1-cyclooctene, is generally obtained in the form of an (E,Z)-mixture in the course of its synthesis by hydroformylation of 1,5-cyclooctadiene, in other words the C=C double bond may be both E- and Z-configured, although a mixture in which the Z configuration predominates is generally present. However, it may even be desirable to use the E- or Z-configured form in pure substance.

The quantities in which the hydroformylation products according to the invention are used in perfume compositions are between 0.001 and 70% by weight, based on the mixture as a whole. The hydroformylation products according to the invention and corresponding compositions may be used both for perfuming cosmetic preparations, such as lotions, creams, shampoos, soaps, salves, powders, aerosols, toothpastes, mouthwashes, deodorants, and in extract perfumery. They may also be used for perfuming technical products and detergents and cleaning compositions, fabric softeners, textile treatment compositions and tobacco. For perfuming these various products, the compositions are added to them in an olfactorily effective quantity, more particularly in a concentration of 0.05 to 2% by weight, based on the product as a whole. However, these values are not intended to represent limits because the experienced perfumist can still obtain effects with lower concentrations or can build up new complexes with even higher concentrations.

The following Examples are intended to illustrate the invention without limiting it in any way.

EXAMPLES

1. Preparation of 4-Cyclooctene Aldehyde

2 Moles (216.36 g) of 1,5-cyclooctadiene (isomer mixture; manufacturer: Acros; gas chromatographic purity: 99%) were introduced into an autoclave together with 1.7 mmoles (1.175 g) of a rhodium catalyst with the formula $Rh(CO)Cl(PPh_3)_2$ and 19 mmoles (5 g) of triphenyl phosphine and reacted with a 1:1 mixture of hydrogen and carbon monoxide with intensive stirring for 5 hours at 100° C. under a pressure of 50 $kg/cm^2$ and in the absence of solvent. For working up, the contents of the reactor were filtered and distilled through a 20 cm Vigreux column. Fractionation into educt, monoaldehyde (4-cyclooctene aldehyde) and dialdehyde was carried out in a spinning band column. 110 g of 4-cyclooctene aldehyde (boiling point: 35° C./0.06 mbar) were obtained together with 12 g of cyclooctane-1,5-dialdehyde (boiling point: 101° C./0.06 mbar).

2. Application Examples

2.1. Citrus composition

| Position | Parts by weight | Ingredient |
|---|---|---|
| 1 | 45 | Citral AR |
| 2 | 80 | Geranonitrile |
| 3 | 15 | Citronellal |
| 4 | 300 | Orange oil, dist. white |
| 5 | 250 | Orange oil, sweet |
| 6 | 10 | Aldehyde C 08 |
| 7 | 10 | Aldehyde C 10 |
| 8 | 70 | Terpineol |
| 9 | 30 | Phenyl ethyl alcohol |
| 10 | 10 | Geranyl acetate |
| 11 | 2 | Dihydroisojasmonate |
| 12 | 70 | Hexyl cinnamaldehyde, alpha |
| 13 | x | Dipropylene glycol (DPG) |
| 14 | 5 | Peranat* |
| 15 | 8 | Aldehyd 11-11* |
| 16 | 10 | Herbavert* |
| 17 | 50 | Melusat* |
| 18 | 30 | Cyclohexyl salicylat* |
| 19 | y | 4-Cyclooctene aldehyde, 1% in DPG |
| | 1000 | |

The products marked with an asterisk are commercial products of Henkel KGaA (Düsseldorf).

Two variants of the composition were investigated:

| | Parts by weight x | Parts by weight y |
|---|---|---|
| Variant 1 | 3 | 5 |
| Variant 2 | 2 | 0 |

Variant 1 was distinguished from variant 2 by the fact that the citrus aroma was found to be more natural, more rounded, more harmonic, more intense in odor and cleaner. By contrast, variant 2 appeared unclean and bitter and was more reminiscent of the odor of lemon pips.

2.2. Raspberry aroma composition

| Position | Parts by weight | Ingredient |
|---|---|---|
| 1 | 10 | Methyl naphthyl ketone, cryst. |
| 2 | 1 | Hexenyl acetate |
| 3 | 1 | Allyl heptanoate |
| 4 | 2 | Amyl butyrate |
| 5 | 9 | Aldehyde C 16 so-called |
| 6 | 2 | Frambinone methyl ether |
| 7 | 80 | Oxyphenylone |

-continued

2.2. Raspberry aroma composition

| Position | Parts by weight | Ingredient |
| --- | --- | --- |
| 8 | 2 | Anisyl acetate |
| 9 | 10 | Styrolyl acetate |
| 10 | 10 | Citronellol, pure |
| 11 | 1 | DMBCA (dimethyl benzyl carbinyl acetate) |
| 12 | 0.5 | Floraline Jasmin 73 |
| 13 | 30 | Benzyl acetate |
| 14 | 10 | Dihydroisojasmonate |
| 15 | 2 | Isoraldein 70 |
| 16 | 5 | Ionone pure 100 |
| 17 | 30 | Vanillin |
| 18 | 2 | Maltol |
| 19 | 5 | Methyl cinnamate |
| 20 | 0.5 | Jasmacyclat* |
| 21 | 1 | Herbavert* |
| 22 | 5 | Floramat* |
| 23 | 30 | Cyclohexyl salicylat* |
| 24 | x | Dipropylene glycol (DPG) |
| 25 | y | 4-Cyclooctenaldehyde 1% in DPG |
|  | 1000 |  |

The commercial products marked with an asterisk are perfumes of Henkel KGaA.

Two variants of the composition were investigated:

|  | Parts by weight x | Parts by weight y |
| --- | --- | --- |
| Variant 3 | 749 | 751 |
| Variant 4 | 2 | 0 |

Variant 3 was distinguished from variant 4 by a more natural, fresher and fruitier raspberry note. Even after 24 hours, its strong and fresh green note still had the same intensity of odor emanating from the sniffing strip. In addition, the perfume spread very intensively and quickly in the test room. By contrast, variant 4 was non-typical, faint and flat in its effect, did not have any room effect and, after 24 hours, could only be detected as a raspberry ketone/vanillin note.

What is claimed is:

1. A method of providing a fragrance to a composition, said method comprising:
   (a) providing a composition; and
   (b) adding a fragrance-providing effective amount of an aldehyde to the composition, wherein the aldehyde is prepared by hydroformylation of a cyclooctadiene, with the proviso that the aldehyde is not a cyclooctane aldehyde.

2. The method according to claim 1, wherein the aldehyde comprises 4-cyclooctene aldehyde.

3. The method according to claim 1, wherein the aldehyde is added in an amount of from about 0.001 to about 70% by weight, based on the combined weight of the composition and aldehyde.

4. The method according to claim 2, wherein the aldehyde is added in an amount of from about 0.001 to about 70% by weight, based on the combined weight of the composition and aldehyde.

5. The method according to claim 1, wherein the aldehyde is prepared by hydroformylation of a cyclooctadiene at a temperature of about 100° C. and at a pressure of about 50 kg/cm$^2$.

6. The method according to claim 1, wherein the composition is selected from the group consisting of cosmetic preparations, detergents, cleaning compositions, fabric softeners, textile treatment compositions and tobacco.

7. The method according to claim 2, wherein the composition is selected from the groups consisting of cosmetic preparations, detergents, cleaning compositions, fabric softeners, textile treatment compositions and tobacco.

8. A method of enhancing fragrance characteristics of a composition, said method comprising:
   (a) providing a composition comprising one or more fragrant components;
   (b) providing an aldehyde prepared by hydroformylation of a cyclooctadiene, with the proviso that the aldehyde is not a cyclooctane aldehyde; and
   (c) combining the composition and a fragrance-enhancing effective amount of the aldehyde.

9. The method according to claim 8, wherein the aldehyde comprises 4-cyclooctene aldehyde.

10. The method according to claim 8, wherein the aldehyde is added in an amount of from about 0.001 to about 70% by weight, based on the combined weight of the composition and aldehyde.

11. The method according to claim 9, wherein the aldehyde is added in an amount of from about 0.001 to about 70% by weight, based on the combined weight of the composition and aldehyde.

12. The method according to claim 8, wherein the aldehyde is prepared by hydroformylation of a cyclooctadiene at a temperature of about 100° C. and at a pressure of about 50 kg/cm$^2$.

13. The method according to claim 8, wherein the composition is selected from the group consisting of cosmetic preparations, detergents, cleaning compositions, fabric softeners, textile treatment compositions and tobacco.

14. The method according to claim 9, wherein the composition is selected from the groups consisting of cosmetic preparations, detergents, cleaning compositions, fabric softeners, textile treatment compositions and tobacco.

* * * * *